United States Patent [19]

Edwards et al.

[11] Patent Number: 4,496,776

[45] Date of Patent: Jan. 29, 1985

[54] EPOXIDE ISOMERIZATION PROCESS

[75] Inventors: Charles L. Edwards; Stanley E. Wilson, both of Houston, Tex.

[73] Assignee: Shell Oil Company, Houston, Tex.

[21] Appl. No.: 522,130

[22] Filed: Aug. 11, 1983

[51] Int. Cl.³ .............................................. C07C 35/18
[52] U.S. Cl. ................................................... 568/827
[58] Field of Search ............................... 568/827, 783

[56] References Cited

U.S. PATENT DOCUMENTS 4,306,099  12/1981  Fetizon et al. ...................... 568/827

OTHER PUBLICATIONS

Eschinasi, E. H., *Israel Journal of Chemistry*, vol. 6, pp. 713–721, (1968).
*Chemical Abstract*, 70:78165x.

*Primary Examiner*—Werren B. Lone

[57] ABSTRACT

Di-, tri- and tetra-substituted epoxides are isomerized to allylic alcohols in the presence of a metal alkoxide catalyst in which the metal is selected from early transition metals of Groups IVA and VA and in the absence of a solvent.

12 Claims, No Drawings

EPOXIDE ISOMERIZATION PROCESS

BACKGROUND OF THE INVENTION

1. Field of the Invention

The present invention relates to the isomerization of certain epoxides to their corresponding allylic alcohols.

2. Description of the Prior Art

It is known from Eschinasi, E. H., *Israel Journal of Chemistry*, 6, pages 713–721 (1968) to use aluminum isopropoxide for the rearrangement of epoxides to allylic alcohols. However, this reaction has been found to be very slow, giving poor conversions and yields of the desired alcohols under practical reaction times. By contrast, it has been found that certain other metal alkoxides give much faster reactions with good conversion and very good selectivity to the desired alcohols.

SUMMARY OF THE INVENTION

The present invention is directed to a process for the preparation of allylic alcohols which comprises isomerizing a di-, tri or tetra-substituted epoxide in the presence of a metal alkoxide catalyst in which the metal is selected from early transition metals of Groups 1VA and VA of the Periodic Table of Elements and in the absence of a solvent.

The catalyst is a metal alkoxide in which the metal is selected from an early transition metal of Groups 1VA or VA of the Periodic Table of Elements, e.g. Ti, Zr, Ta, V and the like. Preferably, the metal is selected from titanium, zirconium or tantalum. While the alkyl portion of the alkoxide can be any lower alkyl group, e.g. containing from about 1 to about 7 carbon atoms, preferably the alkyl portion contains from about 2 to 4 carbon atoms. For example, the metal alkoxide can be titanium isopropoxide (Ti(O-iProp)$_4$), zirconium n-butoxide (Zr(O-nBu)$_4$), tantalum ethoxide (Ta(O-Et)$_5$), and the like, including metal alkoxides coordinated with the alcohol used in making the alkoxide, e.g. Zr(O-nBu)$_4$.nBuOH. Good results have been obtained with zirconium n-butoxide.

The metal alkoxide catalysts are known materials prepared by conventional methods of making metal alkoxides from reaction of the corresponding alkanol with the desired early transition metal of Group 1VA or VA described above.

The epoxides which can be isomerized by the process of the invention are di-, tri- and tetra-substituted epoxides known in the art and containing the oxygen atom attached to two adjacent carbon atoms. Preferably, both of these adjacent carbon atoms are not also part of a carbocyclic ring. These epoxides are readily prepared by conventional procedures known in the art for the epoxidation of aliphatic and cycloaliphatic mono- and non-conjugated polyolefins with e.g. hydrogen peroxide or hydrocarbyl hydroperoxides, preferably in the presence of various metal catalysts.

As examples of the olefins to prepare di-, tri- and tetrahydrocarbyl substituted epoxides, there can be used such substituted diverse materials as:

(a) Aliphatic olefins, such as propylene, butenes, isobutene, hexenes, 4-methyl-2-pentene, etc;

(b) Cycloolefins, for example, cyclopentane, cyclohexane, cyclooctene, etc;

(c) Alkyl and alkenyl cycloolefins, for example, methylcyclohexene, methylcyclopentene, vinylcyclohexene;

(d) Compounds having a plurality of olefinic double bonds, unconjugated, for example, 1,5-cyclooctadiene, 1,5,9-cyclododecatriene, 1,4-cyclohexadiene, cyclohexadiene;

(e) Terpenes, for example, p-menthadienes such as terpinolene, terpinenes, etc.

For example, the epoxide is a tetra-substituted olefinic epoxide in which one carbon of the olefinic group is part of a carbocyclic ring so that the resulting alcohol function is tertiary and attached to the ring. Preferably, the epoxide is a terpenoid epoxide, i.e. one prepared by epoxidation of a terpene, including monocyclic, bicyclic and acyclic terpenes, for example an epoxide prepared from epoxidation of a p-menthadiene and, especially terpinolene epoxide.

The isomerization process of the invention is conducted in the absence of added solvent because usual solvents, such as water, alcohols and hydrocarbons inhibit the reaction.

The isomerization process of the invention is preferably conducted by adding the metal alkoxide catalyst to the epoxide at ambient temperatures in an inert atmosphere, heating the reaction mixture to the desired temperature until the desired degree of conversion has been completed, cooling the reaction mixture and recovering the desired allylic alcohol product by conventional techniques., such as distillation, extraction and the like.

The rate of reaction varies somewhat with the catalyst concentration so that although a catalyst concentration of from about 0.05 to about 5 mole percent per mole of epoxide can be used, it is preferable to use from about 1 to about 2 mole percent of catalyst per mole of epoxide reactant.

The rate of conversion and selectivity to the desired product alcohol varies with the temperature of the reaction under normal pressures. A reaction temperature in the range of from about 100° C. to about 170° C. can be used but a temperature in the range of from about 135° C. to about 155° C. and especially from about 130° C. to about 150° C. gives high conversion in relatively short reaction times.

The present invention is advantageous as a process to isomerize epoxides in high conversion and very good selectivity with lower reaction times.

The product allylic alcohols are known in the art and have application in organic synthesis, for examples as intermediates to the corresponding saturated alcohols, unsaturated halides, halo-substituted allyl alcohols, and the like. The alcohols derived by isomerization of epoxides made from terpenes can also have application in the perfumery industry. In particular, terpinene-4-ol is an important constituent of many so called "essential" oils and has similar utility.

ILLUSTRATIVE EMBODIMENTS

The following Embodiments are presented for the purpose of illustrating the invention and should not be regarded as limiting it in any way.

All reactions were conducted by addition of catalyst to a N$_2$-filled reaction vessel containing the terpinolene 4,7-epoxide at 25° C. The reaction vessel used was a four neck round bottom flask fitted with a N$_2$ inlet, reflux condenser, sampling tube and thermometer. The reflux condenser was connected to a N$_2$ bubbler which was capable of maintaining the unit at one atmosphere of N$_2$. The reaction mixture was heated to the desired reaction temperature at which time aliquots were withdrawn at specified periods and analyzed by GLC. A ⅛"×6' 10% SP-1000 on 100/120 Chromosorb WAW column was used for quantitative analysis.

Embodiment 1

To 11 g of terpinolene 4,7-epoxide was added under nitrogen a single portion of 0.408 g of titanium isopropoxide at 25° C. producing a clear pale gold-colored solution. The reaction mixture was heated at 110°–120° C. for 18 hours at which time the solution was orange-colored and contained water as second immiscible liquid phase. After cooling to 25° C. the mixture was analyzed by gas-liquid chromatography and found that dipentene-4-ol had been produced at 75% conversion with 82% selectivity. Distillation of the crude reaction mixture gave a 51% yield of dipenten-4-ol, b.p. 73° C. (0.4 mm).

Embodiments 2–7

Following procedures similar to those described in Embodiment 1 above, terpinolene 4,7-epoxide was treated with various Group 1V and V metal alkoxides to give dipenten-4-ol.

| Embodiment | Metal Alkoxide | Mole % | Time Hours | Temp. °C. | % Conversion of Epoxide | Selectivity to Dipenten-4-ol |
|---|---|---|---|---|---|---|
| 2 | Ta(OEt)$_5$ | 1 | 17 | 115 | 82 | 78 |
| 3 | Ta(OEt)$_5$ | 2 | 1.5 | 150 | 86 | 73 |
| 4 | Zr(O—nBu)$_4$ | 1 | 14 | 125 | 90 | 70 |
| 5 | Zr(O—nBu)$_4$ | 2 | 2 | 150 | 88 | 83 |
| 6 | Zr(O—nBu)$_4$.nBuOH | 2 | 12 | 130 | 74 | 85 |
| 7 | Ti(O—iProp)$_4$ | 2 | 15 | 110 | 66 | 79 |

What is claimed is:

1. A process for the preparation of allylic alcohols which comprises isomerizing a di-, tri- or tetrahydrocarbyl-substituted epoxide in the presence of a metal alkoxide catalyst in which the metal is selected from early transition metals of Groups 1VA and VA of the Periodic Table of Elements and in the absence of a solvent.

2. A process according to claim 1 wherein the metal is selected from titanium, zirconium or tantalum.

3. A process according to claim 2 wherein in the metal alkoxide the alkyl portion contains from about 2 to about 4 carbon atoms.

4. A process according to claim 3 wherein the metal alkoxide is titanium isopropoxide or zirconium n-butoxide.

5. A process according to claim 4 wherein the epoxide is a tetra-substituted olefinic epoxide in which at least one carbon atom of the olefinic group is part of a carbocyclic ring so that the resulting alcohol function is tertiary and attached to the ring.

6. A process according to claim 4 wherein the epoxide is a terpenoid epoxide.

7. A process according to claim 6 wherein the epoxide is prepared from a p-menthadiene.

8. A process according to claim 7 wherein the epoxide is terpinolene epoxide.

9. A process according to claim 1 wherein the temperature is in the range of from about 100° C. to about 170° C.

10. A process according to claim 2 wherein the temperature is in the range of from about 135° C. to about 150° C.

11. A process according to claim 1 wherein the metal alkoxide catalyst is used in a concentration of from about 0.05 to about 5 mole percent per mole of epoxide.

12. A process according to claim 2 wherein the metal alkoxide catalyst is used in a concentration of from about 1 to about 2 mole percent per mole of epoxide.

* * * * *